US012570930B2

(12) United States Patent
Bhamla et al.

(10) Patent No.: US 12,570,930 B2
(45) Date of Patent: Mar. 10, 2026

(54) METHODS AND SYSTEMS FOR SOLVENT-FREE CLEANING OF SURFACES

(71) Applicant: Georgia Tech Research Corporation, Atlanta, GA (US)

(72) Inventors: M. Saad Bhamla, Atlanta, GA (US); Katherine R. Burgener, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 226 days.

(21) Appl. No.: 17/908,117

(22) PCT Filed: Mar. 3, 2021

(86) PCT No.: PCT/US2021/020620
§ 371 (c)(1),
(2) Date: Aug. 30, 2022

(87) PCT Pub. No.: WO2021/178506
PCT Pub. Date: Sep. 10, 2021

(65) Prior Publication Data
US 2023/0018766 A1      Jan. 19, 2023

Related U.S. Application Data

(60) Provisional application No. 62/984,322, filed on Mar. 3, 2020.

(51) Int. Cl.
*C11D 3/37* (2006.01)
*A61L 12/06* (2006.01)
(Continued)

(52) U.S. Cl.
CPC ............ *C11D 3/373* (2013.01); *A61L 12/063* (2013.01); *B08B 7/00* (2013.01); *C11D 3/0078* (2013.01)

(58) Field of Classification Search
CPC ......... C11D 3/373; C11D 3/0078; C11D 3/37; A61L 12/063; A61L 12/08; A61L 12/14; B08B 7/00
See application file for complete search history.

(56) References Cited

U.S. PATENT DOCUMENTS

| | | | | | |
|---|---|---|---|---|---|
| 5,370,744 | A | * | 12/1994 | Chowhan | .............. A61L 12/145 134/42 |
| 2004/0091603 | A1 | * | 5/2004 | Priewe | ................. A61L 31/146 427/2.24 |

(Continued)

OTHER PUBLICATIONS

Halake, Kantappa, "IStrategies for Fabrication of Hydrophobic Porous Materials Based on Polydimethylsiloxane for Oil-Water Separation", Macromolecular Research, vol. 27, ("Halake Reference") (Year: 2019).*

(Continued)

*Primary Examiner* — Kaj K Olsen
*Assistant Examiner* — Arlyn I Rivera-Cordero
(74) *Attorney, Agent, or Firm* — TROUTMAN PEPPER LOCKE LLP; Ryan A. Schneider; Harrison D. Lawrence

(57) ABSTRACT

An exemplary embodiment of the present disclosure provides solvent-free cleaning systems and methods, the systems and methods comprise a polymer substrate having a crosslinked matrix positioned on at least one surface of the polymer substrate, wherein the crosslinked matrix is configured to absorb particulates from a surface of a material when placed in direct contact.

30 Claims, 7 Drawing Sheets

(51) Int. Cl.
    B08B 7/00           (2006.01)
    C11D 3/00           (2006.01)

(56)               References Cited

U.S. PATENT DOCUMENTS

| | | | |
|---|---|---|---|
| 2010/0212702 A1* | 8/2010 | Hamada | H01L 21/02068 |
| | | | 134/115 R |
| 2012/0138819 A1* | 6/2012 | Pugh | A45C 11/005 |
| | | | 250/455.11 |
| 2015/0020849 A1* | 1/2015 | Harrison | B08B 3/08 |
| | | | 134/4 |
| 2017/0283062 A1* | 10/2017 | Childress | B08B 5/04 |
| 2018/0312784 A1* | 11/2018 | Izadi | B08B 7/0028 |

OTHER PUBLICATIONS

International Search Report and Written Opinion from application No. PCT/US2021/020620 dated Jul. 23, 2021.
Sigma-Aldrich, "Slygard 184" https://www.sigmaaldrich.com/catalog/product/ALDRICH/761028?lang=en&region=US.
Calo, et al., "Biomedical Applications of Hydrogels: A review of Patents and Commerical Products," 2015 European Polymer Journal vol. 65 pp. 252-267.
"What to Look for When Comparing UV Sterilization Devices," HepaCart, Nov. 27, 2018.
Kopecek, "Hydrogel Biomaterials: A Smart Fugure?" 2007 Biomaterials vol. 28, No. 34 pp. 5185-5192.
"Silicon Elastomer, Slygard 184 Clear Kit, Krayden," Apr. 29, 2021, https://us.vwr.com/store/product 24180375/slygard-184-clear-kit-krayden.

* cited by examiner

200

202

106

108

106

METHODS AND SYSTEMS FOR SOLVENT-FREE CLEANING OF SURFACES

CROSS-REFERENCE TO RELATED APPLICATIONS

This application claims the benefit of U.S. Provisional Application Ser. No. 62/984,322, filed on 3 Mar. 2020, which is incorporated herein by reference in its entirety as if fully set forth below.

FIELD OF THE DISCLOSURE

The various embodiments of the present disclosure relate generally to solvent-free cleaning methods and systems for removing particulates and contaminants from the surface of materials, and more particularly to solvent-free cleaning methods and systems for removing particulates and contaminants from the surface of contact lenses.

BACKGROUND

Cleaning hydrogel materials with solutions and chemicals can be effective at removing some contaminants, but these techniques often are not sufficient to remove the micron and sub-micron solid particulate matter, such as dust or pollutants. Hydrogel materials used in various medical applications require the most sterile surfaces and inadequate cleaning of the smaller particulates can be harmful to the end-user of the hydrogel. For example, medical-based hydrogels such as contact lenses or tissue scaffolds are applied directly on a user's organ, such as the eye, and can be susceptible to collecting solid particulates from the organ's internal surroundings and its environment. These particulates may include proteins and lipids from the body as well as foreign substances such as cosmetics, soaps, airborne dust, pollution, smog, pollen, cigarette smoke, diesel exhaust and others. Typical cleaning methods and systems for contact lenses use solution alone or in combination with mechanical rubbing between the fingers. Rub-free methods require harsh chemicals that can result in weakening or damaging of the hydrogel surface and often fails to completely remove all micron and sub-micron particulates. Therefore, there is a great need for effective methods and systems that can assist in removing all solid particulate matter, regardless of size, from a hydrogel surface without use of solvents, high shear forces, or any other damage to the hydrogel.

BRIEF SUMMARY

The present disclosure relates to solvent-free cleaning systems and methods. An exemplary embodiment of the present disclosure provides a system having a polymer substrate having a crosslinked matrix. The crosslinked matrix can be positioned on at least one surface of the polymer substrate. The crosslinked matrix can be configured to absorb, transfer, remove, and/or extract particulates from a surface of a material when placed in direct contact.

In any of the embodiments disclosed herein, the polymer substrate can comprise an inert biocompatible polymer.

In any of the embodiments disclosed herein, the inert biocompatible polymer can be selected from the group consisting of polyethylbenzene, polydimethylsiloxane (PDMS), polyglycolic acid (PGA), poly-L-lactic acid (PLA), polycaprolactive, polyhydroxybutyrate, polyhydroxyvalerate, polydioxanone, polycarbonate, and polyanhydride, polycaprolactone (PCL), polydioxanone (PDO), polybutyrolactone (PBL), polyvalerolactone (PVL), poly(lactide-co-glycolide) (PLGA), and combinations thereof.

In any of the embodiments disclosed herein, the polymer substrate can comprise a Young's modulus of about 0.5 MPa.

In any of the embodiments disclosed herein, the polymer substrate can comprise a Young's modulus from about 0.01 MPa to about 0.5 MPa.

In any of the embodiments disclosed herein, the crosslinked matrix comprises micron and/or sub-micron pores.

In any of the embodiments disclosed herein, the crosslinked matrix can be further configured to absorb particulates from the surface of a dry material.

In any of the embodiments disclosed herein, the crosslinked matrix can be further configured to absorb particulates from the surface of a moist material.

In any of the embodiments disclosed herein, the particulates can be removed from the surface of the material without damage to the material.

In any of the embodiments disclosed herein, the material can comprise a hydrogel.

In any of the embodiments disclosed herein, the hydrogel can comprise a contact lens, a tissue scaffold, a wound dressing, a drug delivery system, and combinations thereof.

In any of the embodiments disclosed herein, the system can further comprise removing particulates from the surface of a contact lens when in direct contact with the crosslinked matrix of the polymer substrate.

In any of the embodiments disclosed herein, the particulates can comprise micron and/or sub-micron particulates.

In any of the embodiments disclosed herein, at least a portion of the polymer substrate can be translucent.

In any of the embodiments disclosed herein, the system can further comprise a light source positioned in and/or near the polymer substrate. The light source can be configured to emit light on at least a portion of the surface of the material.

In any of the embodiments disclosed herein, the light source can emit disinfecting light to disinfect at least a portion of the surface of the material.

An exemplary embodiment of the present disclosure provides a solvent-free cleaning method. The method can comprise contacting a surface of a material to a polymer substrate and transferring particulates from the surface of the material to the crosslinked matrix of the polymer substrate. The polymer substrate can have a crosslinked matrix positioned on at least one surface of the polymer substrate.

In any of the embodiments disclosed herein, transferring the particulates to the crosslinked matrix from the surface of the material does not damage the material.

In any of the embodiments disclosed herein, the method can further comprise emitting disinfecting light on at least a portion of the surface of the material.

An exemplary embodiment of the present disclosure provides a method for cleaning a contact lens. The method can comprise contacting at least a portion of the contact lens to a polymer substrate and transferring particulates from the surface of the contact lens to the crosslinked matrix of the polymer substrate. The polymer substrate can have a crosslinked matrix positioned on at least one surface of the polymer substrate.

In any of the embodiments disclosed herein, transferring the particulates to the crosslinked matrix from the surface of the material does not damage the contact lens.

In any of the embodiments disclosed herein, the method can further comprise emitting disinfecting light on at least a portion of the surface of the contact lens.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIGS. 3B and 3C show images collected with a stereo microscope and FIG. 3D shows an image collected with a scanning electron microscope (SEM).

DETAILED DESCRIPTION

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

Figure 1:
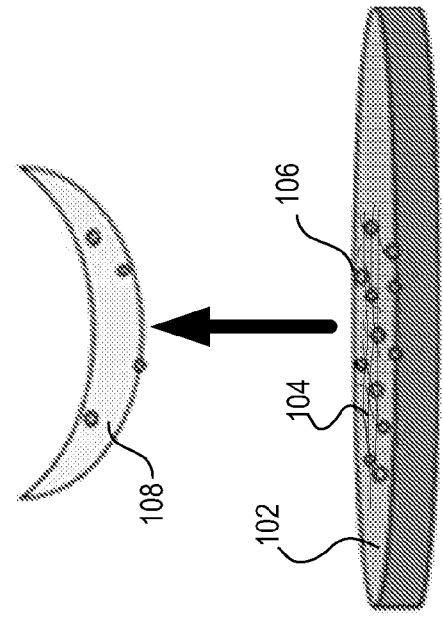
FIG. 1 shows renderings of an exemplary embodiment of a solvent-free cleaning method and system, in accordance with an exemplary embodiment of the present disclosure.
Figure 1:
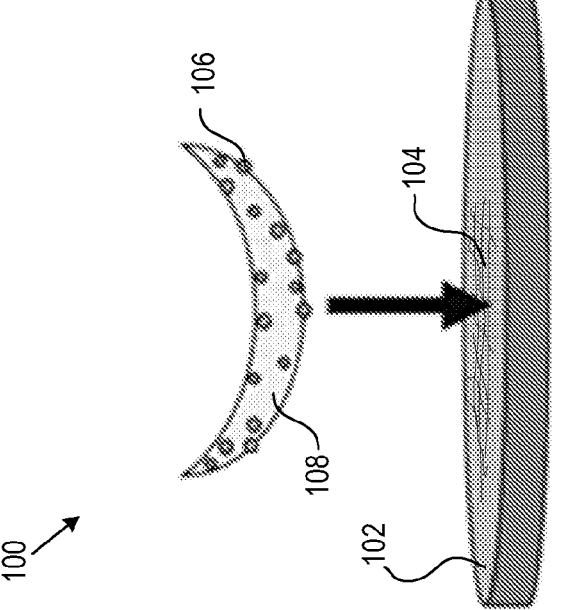

As shown in FIG. 1, an exemplary embodiment of the present disclosure provides a solvent-free cleaning system 100. In some embodiments, solvent-free cleaning system 100 includes a polymer substrate 102 that has a crosslinked matrix 104 configured to absorb, transfer, remove, and/or extract particulates 106 from a surface of a material 108 when the material is directly in contact with polymer substrate 102.

In some embodiments, polymer substrate 102 can be made of, at least in part, by an inert biocompatible polymer. In certain embodiments, polymer substrate 102 can also include two or more biocompatible polymer having similar or different properties. Polymer substrate 102 biocompatible polymers can include polyethylbenzene, polydimethylsiloxane (PDMS), polyglycolic acid (PGA), poly-L-lactic acid (PLA), polycaprolactive, polyhydroxybutyrate, polyhydroxyvalerate, polydioxanone, polycarbonate, and polyanhydride, polycaprolactone (PCL), polydioxanone (PDO), polybutyrolactone (PBL), polyvalerolactone (PVL), poly (lactide-co-glycolide) (PLGA), and combinations thereof. As would be appreciated by those of skill in the art, any biocompatible polymer can be used in the solvent-free cleaning system and method. In some embodiments, polymer substrate 102 can be any thermosetting biocompatible polymer.

As would be appreciated, biocompatible polymers with low surface energy and high elasticity such that mechanical stresses between polymer substrate 102 and material 108 can be minimized. Any type of biocompatible polymer may be able to form an intimate contact with the surface of material 108 and generate strong interfacial interactions with particulates 106 on the surface of material 108. In general, polymer substrate 102 having a stronger interfacial interaction with particulates 106 than the interfacial interaction between particulates 106 and material 108 can result in increased absorption of particulates onto and/or into polymer substrate 102 and crosslinked matrix 104. Interaction forces can include any known intermolecular force, such as Van der Waals forces, hydrogen bonding, ionic bonding, ion-induced dipole forces, and/or ion-dipole forces.

In any of the embodiments disclosed herein, polymer substrate 102 can be made by mixing an elastomer and a curing agent prior to adding heat and/or light to cure at least a portion of the elastomer and curing agent mixture. Variation in the elastomer to curing agent ratio can change the properties of polymer substrate 102. In some embodiments, increasing the elastomer concentration while maintaining the curing agent concentration can generate polymer substrate 102 with a decreased Young's modulus. For example, polymer substrate 102 with a Young's modulus of about 0.5 MPa or lower may provide enhanced particulate absorption properties. As would be appreciated, polymer substrate 102 having a lower Young's modulus may increase the stickiness of the surface of polymer substrate 102. In any embodiment herein, polymer substrate 102 may have a Young's modulus below about 0.5 MPa (e.g., less than 0.45 MPa, less than 0.40 MPa, less than 0.35 MPa, less than 0.30 MPa, less than 0.25 MPa, less than 0.20 MPa, less than 0.15 MPa, less than 0.10 MPa, less than 0.08 MPa, less than 0.06 MPa, less than 0.04 MPa, less than 0.03 MPa, less than 0.02 MPa, less than 0.01 MPa, or any value between, e.g., less than 0.22 MPa or 0.07 MPa).

In some embodiments, polymer substrate 102 having two or more inert biocompatible polymer materials, the Young's modulus of polymer substrate 102 may vary depending on the localized concentration of a certain biocompatible polymer present. For instance, polymer substrate 102 may have a polyethylbenzene and PDMS composition and may have different Young's modulus at different locations along the surface of polymer substrate 102. As would be appreciated by one of skill in the art, different polymer compositions and different ranges of elastomer to curing agent may vary the Young's modulus. As such, the Young's modulus of solvent-free cleaning system and method 100 may range from about 0.01 MPa to about 0.5 MPa (e.g., from about 0.01 MPa to about 0.05 MPa, from about 0.05 MPa to about 0.1 MPa, from about 0.1 MPa to about 0.15 MPa, from about 0.15 MPa to about 0.2 MPa, from about 0.2 MPa to about 0.25 MPa, from about 0.25 MPa to about 0.3 MPa, from about 0.3 MPa to about 0.35 MPa, from about 0.35 MPa to about 0.4 MPa, from about 0.4 MPa to about 0.45 MPa, from about 0.45 MPa to about 0.5 MPa, or any range therewithin, e.g., from about 0.17 MPa to about 0.32 MPa).

In any of the embodiments herein, polymer substrate 102 may be molded to any shape so as to allow for adequate direct contact between polymer substrate 102 and material 108. In some embodiments, polymer substrate 102 can be flat and of a dimension that can allow for a large piece of material to be placed in contact over the length of the materials dimension. In some embodiments, a large piece of material may be moved over polymer substrate 102 such that different areas of material contact multiple regions of polymer substrate 102. In certain embodiments, polymer substrate may be molded into a convex or concave shape such that a curved material, such as a contact lens, may be placed in direct contact along the curve of the contact lens. In yes other embodiments, polymer substrate 102 can be flexible and capable of bending easily without breaking, such that flexible polymer substrate 102 may be adapted to conform to any shape or form of material 108.

In some embodiments, solvent-free cleaning system and method 100 may have a crosslinked matrix 104 positioned on at least one surface of polymer substrate 102. Crosslinked matrix 104 may generate one or more pores on the surface of polymer substrate 102 and/or within the interior of polymer substrate 102. As would be appreciated, the variation in biocompatible polymer composition and/or variation in Young's modulus may alter the extent of crosslinking within crosslinked matrix 104 and change the size, shape, and range of pores. Crosslinked matrix 104 can comprise micron and/or sub-micron pores. Crosslinked matrix 104 can be configured to absorb, transfer, remove, and/or extract particulates 106 from a material 108 when material 108 is placed in direct contact with crosslinked matrix 104. As shown in FIG. 1, particulates 106 may transfer from the surface of material 108. In some embodiments, particulates 106 may be trapped on or within the pores of crosslinked matrix 104, resulting in less particulates 106 remaining on the surface of material 108.

In any embodiment, crosslinked matrix 104 may be configured to absorb, transfer, remove, extract, and/or trap particulates from surface of a material that is dry, dehydrated, desiccated, or substantially free of wetting agents and hydrophilic properties. In some embodiments, crosslinked matrix 104 may be configured to absorb, transfer, remove, extract, and/or trap particulates from surface of a material that is moist, damp, watery, or having hydrophilic properties such as hydrogel materials.

Figure 2:
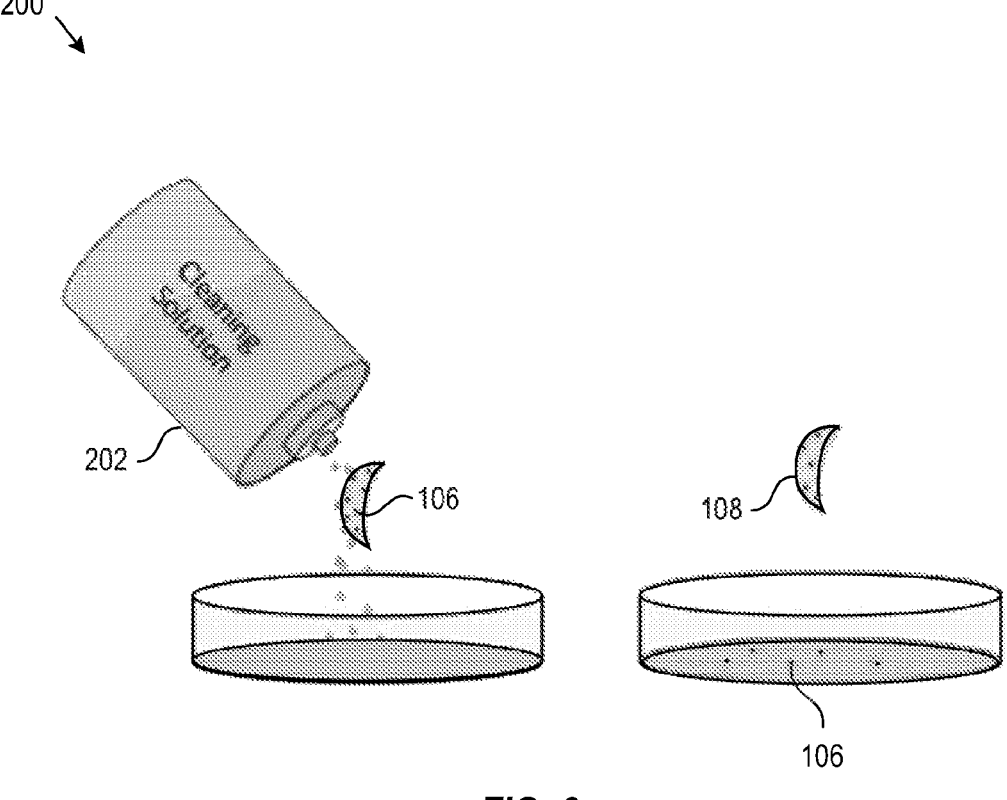
FIG. 2 provides a rendering of solution-based cleaning for removing particulates, in accordance with an exemplary embodiment of the present disclosure.
Figure 3:
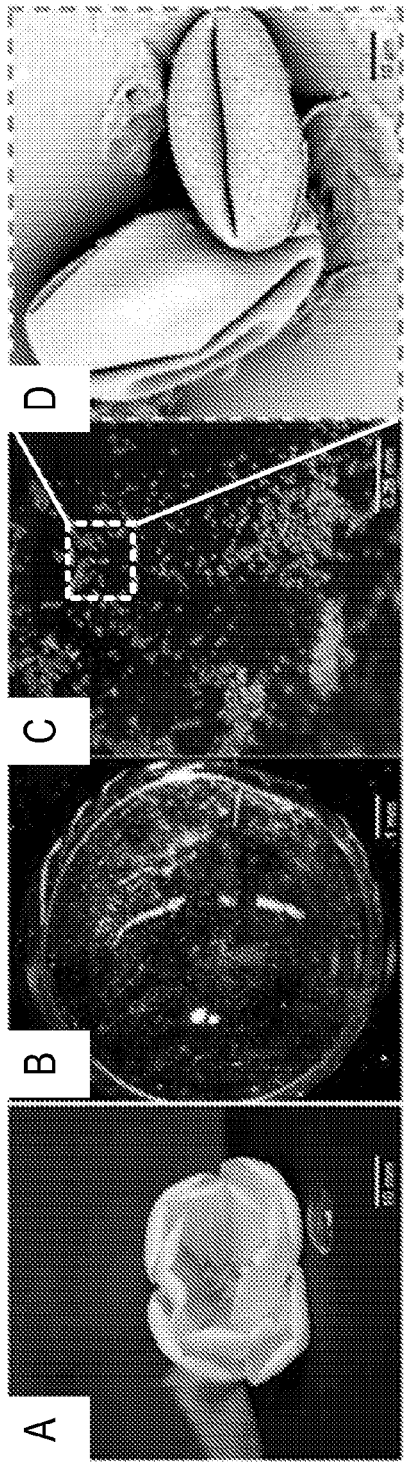
FIGS. 3A-3D provide images of airborne pollutant particulates on the surface of a contact lens, a in accordance with an exemplary embodiment of the present disclosure.

In some embodiments, particulates 106 may be trapped on or within the pores of crosslinked matrix 104 when material 108 is placed in contact with polymer substrate 102 for a short period of time. For instance, as illustrated in FIG. 2, contacting material 108 with polymer substrate 102 for less than about 20 seconds may effectively remove more particulates 106 than when material 108 is rinsed with a cleaning solution 202 or placed within a cleaning solution for similar amounts of time, or even longer. In any embodiment, contacting material 108 to polymer substrate 102 for less than 15 seconds may be effective at removing particulates 106 (e.g., less than 14 seconds, less than 13 seconds, less than 12 seconds, less than 11 seconds, less than 10 seconds, less than 9 seconds, less than 8 seconds, less than 7 seconds, less than 6 seconds, less than 5 seconds, less than 4 seconds, less than 3 seconds, less than 2 seconds, or less than 1 second).

In some embodiments, solvent-free cleaning system and method 100 may be used prior to any other cleaning method used, such as, for example, soaking material 108 in a cleaning solution 202 or rubbing material 108 in combination with cleaning solution 202. In some embodiments, solvent-free cleaning system and method 100 may be used prior to applying material 108 for its intended use. For instance, a user of contact lenses may apply solvent-free cleaning system and method 100 to a contact lens prior to placing the contact lens on the eye. In another example, a user of a tissue scaffold may apply solvent-free cleaning system and method 100 prior to placing the tissue scaffold on the target tissue to ensure particulates are effectively removed and additional solvent is not necessary.

In some embodiments, particulates 106 can be micron particulates ranging from about 1 mm to about 1000 mm. Example micron particulates can include, but are not limited to, pollen and mold spores, lint, fungi, bacteria, wood smoke, cooking smoke, pesticides, herbicides, dust, dust mites, hair, pet dander, auto emission, fiberglass insulation particles, carpet fibers, coal dust, asbestos dust, insecticide, and microbeads. In some embodiments, particulates 106 can be sub-micron particulates ranging from about 10 μm to about 1000 nm. Example sub-micron particulates can include, but are not limited to, viruses, sub-pollen, suspended atmospheric dust, asbestos, smog, oil smoke, tobacco smoke, volatile organic compounds, nanobeads, and nanoparticles.

In any of the embodiments disclosed herein, at least a portion of material 108 can include a hydrogel, such as, for example, a contact lens, a tissue scaffold, a wound dressing, a drug delivery system, or any combination thereof. As would be appreciated, material 108 can also be any rigid material that has particulates, as described above, on the material surface.

In some embodiments, at least a portion of polymer substrate 102 can be translucent or can permit light to illuminate through at least a portion of polymer substrate 102. Light can be beneficial for several reasons, for example, to disinfect the surface of material 108, improve air quality around material 108, reduce mold and/or mildew around material 108, assist in identifying particles on material 108, and/or can be decorative and ornamental. In some embodiments, light emitted from a light source positioned in and/or near polymer substrate 102 can include infrared, visible, and/or ultraviolet light. As would be appreciated, solvent-free cleaning system and method 100 can be configured to absorb, transfer, remove, and/or extract particulates 106 from material 108 to polymer substrate 102 in combination with a light that functions to disinfect, improve air quality, reduce mold and/or mildew, and/or be decorative and ornamental using one or more wavelengths of disinfecting light.

As would be appreciated by those of skill in the art, since the polymer substrates can be molded and sized for any application, such solvent-free cleaning system can be provided within the packaging of a specific material needing to be cleaned, such as, for example, contact lenses. As an example, the solvent-free cleaning system described herein can be included within an individual contact lens package either in the solution with the contact lens or in a separate compartment above or below the individual contact lens package. In some embodiments, removing particulates from a contact lens can be done prior to wearing and/or storing the contact lens. In certain embodiments, it is contemplated that the solvent-free cleaning system can be provided as a stand-alone product that can be used for any type of material needing to be cleaned.

The following examples further illustrate aspects of the present disclosure. However, they are in no way a limitation of the teachings or disclosure of the present disclosure as set forth herein.

EXAMPLES

Example 1: Particulates

Solid pollutants are classified by size as particulate matter (PM). $PM_{2.5}$ particles are airborne pollutants with diameters less than 2.5 μm. Both natural and manufactured air pollutants fall within this size range; common examples of these micro and nano-pollutants are carbon-rich fluffy soot aggregate, cigarette smoke, pollen, mushroom spores, particulates with metallic elements, as well as diesel exhaust (FIGS. 3A-3D). $PM_{2.5}$ pollutants are relevant to ocular health because they decrease tear osmolarity and increase dry eye, ocular irritation, and burning.

Typical soft contact lens pore sizes are on the order of sub-micrometers, with diameters up to 0.2 μm. Large foreign objects (lashes, mascara, debris) do get caught on contact lenses and the conventional cleaning method of rinsing with cleaning solution and rubbing with fingers (RR) appears to work in dislodging them from the hydrogel matrix. Due to their rough nature, smaller bodies (minerals, aerosol pollution) have the potential to embed themselves in the lens, rendering rubbing inadequate and potentially harmful to the surface of the lens.

Recent improvements in the hydrogel polymer matrix of contact lenses have increased the lenses' antimicrobial properties but have not changed the way contact lenses are cleaned (i.e. rubbing the lens or using multi-purpose solutions (MPS)). Some MPS were developed as a 'no-rub' cleaning alternative that disinfected lenses by rinsing and extended soaking overnight. While this cleaning technique has been shown to decrease biofilm activity on lenses, not all MPS solutions are able to remove physical deposits from the lens. Rubbing has been demonstrated as a necessary addition to cleaning regimens due to the ability of the shear forces applied by the fingers to remove pollutants. Prolonged wear of lenses leads to physical fatigue of the lens integrity; constant mechanical stress changes the morphology of the surface and the pore sizes of the lenses. The repetitive motion of blinking can damage the lens, so the shear forces of fingers rubbing across the surface would be expected to also damage the surface of lenses.

Polydimethylsiloxane (PDMS) has many uses due to its physical properties of straightforward fabrication and transparency, though it is used most frequently in microfluidic design and research. PDMS was chosen as the candidate material in this experiment due to its extensive use and testing in research and industry. PDMS is widely and commercially available and its properties are well studied and understood. More specifically, when set, PDMS is a soft, inert, and elastic material with tunable Young's modulus, low autofluorescence, and excellent biocompatibility. The proposed new method of contaminant removal takes advantage of these ideal characteristics. Polymer on polymer pollutant removal (PoPPR) involves pressing a contaminated contact lens onto a surface of PDMS. The PDMS envelops the pollutants on the lens while the hydrophobicity of PDMS prevents the lens from sticking to the PDMS surface. The result is a transfer of pollutants from lens to PDMS, as shown in FIG. 1. The aim of these proof-of-concept experiments was to determine how effective PoPPR is at cleaning physical pollutants from contact lens surfaces and to compare the results to control method, RR.

Examples 2: Contact Lenses

All contact lenses used for experiments were 1-Day Acuvue TruEye+6.0 lenses (Johnson & Johnson Vision, Jacksonville, FL). The lenses were rinsed with Biotrue multi-purpose solution (Bausch & Lomb, Rochester, NY) before running experiments.

Examples 3: PDMS

SYLGARD™ 184 Silicone Elastomer was used to make the PDMS (2646340, Dow). The commercial Sylgard kit contains both the PDMS polymer and the elastomer curing agent. The product suggests mixing a 1:10 ratio of setting agent to polymer. To increase the elasticity of the PDMS, the following ratios were used: 1:30, 1:40, 1:50. Both liquids were combined in 35 mm petri dishes. The average total weight of each experimental sample was approximately 18 g. To ensure an even distribution of setting agent in the polymer, samples were stirred vigorously for five minutes. After mixing the two liquid parts, samples were de-aired using a vacuum desiccator until all bubbles were removed from the mixture. Each sample was cured for at least 24 h at 50° C. in an incubator at 10% humidity.

Examples 4: Pollutants

Populus Tremuloids pollen averages 25-40 μm in diameter and was obtained for pollen removal trials (P7770-500MG, Sigma Aldrich). Fluorescent microbeads with diameters between 1-5 μm were used for the microbead removal experiments (300-45-225, Cospheric). For nanoparticle removal trials, copper indium disulfide/zinc sulfide quantum dots between 5-10 nm in diameter were used (29-8520, Strem Chemicals). All pollutants were suspended in water before application to contact lenses.

Examples 5: Cleaning Experiments

Part a. Controlled Fouling of Lenses

First, clean lenses were polluted with a solution of water and pollutant. The concentration of pollen in water was 0.001 g/mL; the microbead solution had a concentration of 1.225*10-5 g/mL. Pollen and Microbead: Both pollen and microbeads were aerosolized onto the lens with a spray bottle, which released approximately 1 mL of solution every five sprays. Nanoparticle: 0.5 mL of 5.4*10-5 g/mL nanoparticle solution was pipetted onto the lens in order to avoid harmful aerosolization. The concentration of particles deposited on lenses using aerosolization (FIG. 1) or pipetting were distributed throughout the entire lens area as evidenced through visual inspection using a microscope.

Part b. Cleaning Protocol

RR protocol: The lenses were cleaned by rinsing with standard multi-purpose cleaning solution and rubbing the polluted surface between the thumb and index finger (see FIG. 2). Since RR is a qualitative procedure, to maintain consistency between trials, the lens was gently rubbed for five seconds, followed by a rinse for five seconds. The rinsing solution was put in sterile petri dishes. Great care was taken to ensure that all cleaning solution was collected.

PoPPR protocol: The polluted surfaces of lenses were pressed into a sample of clean PDMS. Lenses were only pressed once onto the PDMS surface and peeled away after five seconds of contact.

Part c. Analysis

Figure 4:
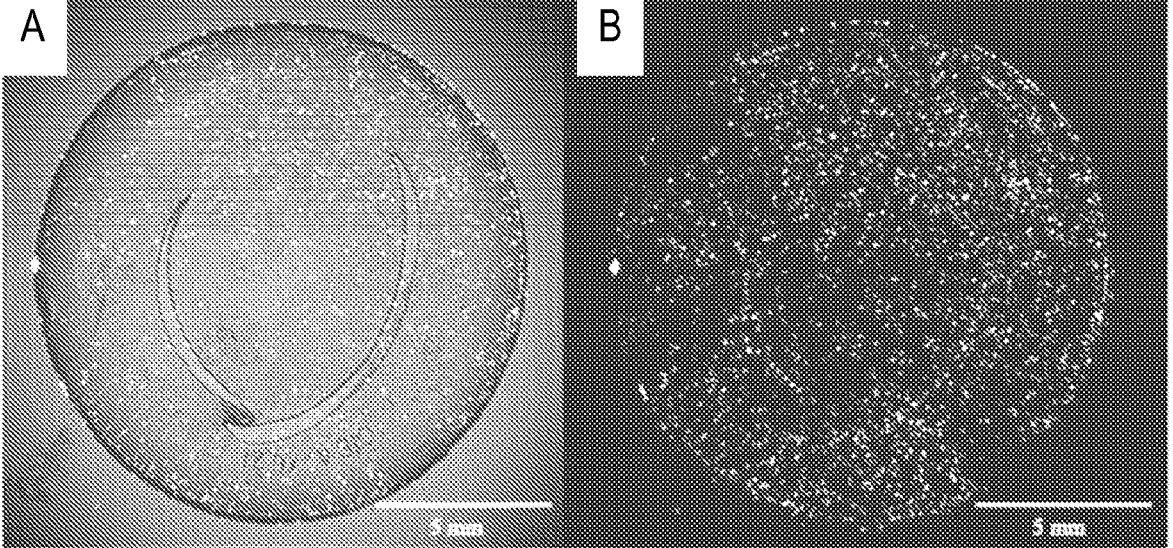
FIGS. 4A and 4B provide fluorescence microscopy images of particulates remaining on a hydrogel surface after treating with either a solution-based cleaning method or a solvent-free cleaning method and system, in accordance with an exemplary embodiment of the present disclosure.

After the cleaning step, the contact lenses were allowed to dehydrate (24 h) and were then sandwiched between two clean glass slides to enable viewing under a microscope. The rinsing solution from RR protocol was allowed to evaporate so that the pollutants were left on the bottom of the petri dishes. As shown in FIG. 4, fluorescent images were taken of the used lens, and either the rinsing solution petri dish or PDMS with a fluorescence microscope. To image the entire surface at 10× magnification, approximately 13, 15, and 30 images were required of the contact lens, petri dish, and PDMS respectively.

Using the 'analyze particles' program on Fiji, pollutants were counted, and the fraction of pollutant removal was calculated. The fraction of pollutant removed was calculated as follows:

$$\text{Fraction Removed} = \frac{n_{removed}}{(n_{removed} + n_{remaining})}$$

where $n_{removed}$ refers to the number of pollutant particles either on the PDMS or in the petri dish and $n_{remaining}$ is the number of pollutant particles on the used lens. It should be noted that the initial number of particles deposited using the controlled fouling step is not measurable as it involves drying the lens to manually count, which renders the cleaning protocol difficult. Thus, all cleaning experiments were performed carefully so that $n_{removed} + n_{remaining}$ could be used as a proxy for the total initial particles.

The cleaning efficiencies of PoPPR and the control (RR) were compared for three different pollutant sizes (25-40 μm, 1-5 μm, 5-10 nm). For all pollutant sizes, at least four trials were conducted for each test to ensure repeatability and reproducibility. Because pollen is not fully fluorescent and its shape is not uniform, each pollen grain on the lens, in solution, or on PDMS, was hand-counted. For this reason, only four trials were conducted. Experimental microbeads are fully fluorescent and were able to be counted with Fiji software, ten trials were deemed sufficient. Nanoparticles are also fluorescent and can be identified and counted using the Fiji software.

To examine the role of PDMS stiffness in cleaning efficiency for PoPPR, three different ratios of PDMS were also tested (1:30, 1:40, and 1:50).

Example 6: Statistical Analysis

Statistical analyses were performed using Statistical Analysis Software (SAS) Version 9.4 (SAS Institute, Cary, NC). The Shapiro-Wilke test was used to assess normality of the data. Wilcoxon (Rank Sums) tests were performed on each pollutant size to assess differences in effectiveness between the cleaning methods. Outliers were identified using the Grubbs test. Standard deviations ($\sigma$), means ($\mu$), mid-ranges (MR), and number of trials (n) for each cleaning method were recorded. Finally, to assess statistical significance between cleaning methods, two-tailed two-sample t-tests were conducted at a 95% level of significance. The means and standard deviations are presented as $\mu \pm \sigma$ below.

Example 7: Pollen Removal

Figure 5:
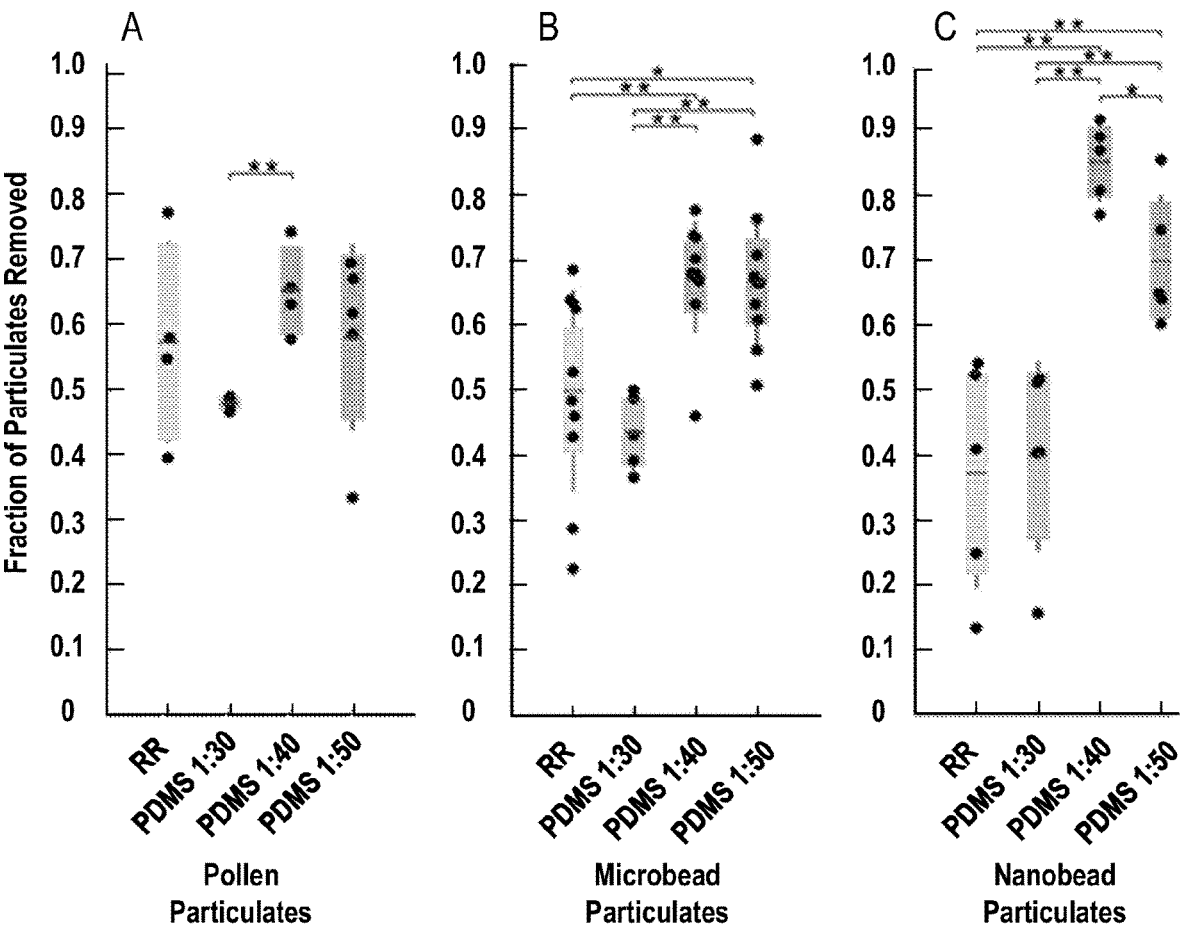
FIGS. 5A-5C show plots of fraction of pollen particulates (FIG. 5A), microbead particulates (FIG. 5B), and nanobead particulates (FIG. 5C) removed from a hydrogel surface after treating with either a solution-based cleaning method or various solvent-free cleaning methods and systems, in accordance with an exemplary embodiment of the present disclosure.

The fraction of pollen removed using the control method (RR) averaged $0.57 \pm 0.2$ (n=4). The mean fractions of pollen removed from PDMS 1:30, 1:40 and 1:50 using the PoPPR method were $0.48 \pm 0.01$ (n=4), $0.65 \pm 0.07$ (n=4), and $0.62 \pm 0.14$ (n=5) (FIG. 5A).

For the removal of pollen from contact lenses, there were no statistical differences in the cleaning methods (p=0.249). The only statistical difference in pollen removal methods was between PDMS 1:30 and 1:40 PoPPR (p=0.0024).

Example 8: Microbead Removal

The mean fraction of microbeads removed from lenses using the RR method was $0.50 \pm 0.16$ (n=10). For the PoPPR trials of PDMS 1:30, 1:40 and 1:50, the mean fractions of pollutant removed were $0.43 \pm 0.06$ (n=5), $0.67 \pm 0.09$ (n=10), and $0.67 \pm 0.11$ (n=10) respectively (FIG. 5B).

Statistical differences were observed between RR and PDMS 1:40 (p=0.006) as well as RR and PDMS 1:50 (p=0.011). PDMS 1:30 results were also different from PDMS 1:40 (p<0.001) and 1:50 PDMS (p<0.001). In the microbead data for PDMS 1:40, there was one significant outlier, but removing the outlier did not change statistical results.

Example 9: Nanoparticle Removal

The RR method resulted in a mean fraction of $0.37 \pm 0.18$ (n=5) for nanoparticle removal. The mean fractions of nanoparticles removed from lenses using the PoPPR methods of PDMS 1:30, 1:40, and 1:50 were $0.40 \pm 0.15$ (n=5), $0.85 \pm 0.06$ (n=5), and $0.70 \pm 0.10$ (n=5) (FIG. 5C).

The following cleaning methods were statistically different: RR and PDMS 1:40 (p<0.001), RR and PDMS 1:50 (p=0.007), PDMS 1:30 and PDMS 1:40 (p<0.001), PDMS 1:30 and PDMS 1:50 (p=0.0055), PDMS 1:40 and PDMS 1:50 (p=0.021).

The PoPPR method was comparable to the RR method for pollen pollutants. FIGS. 5A-5C show the means ($\mu$) and standard deviations ($\sigma$) of the RR method. The large midrange (MR) in RR data (0.2) compared to a smaller MR of PDMS 1:40 data (0.08) indicates that the RR method is not as precise as the PoPPR technique.

The large size of the experimental pollen can explain some of these results. Populus Tremuloids pollen has an average diameter of 25-40 μm which is larger than the average contact lens pore size (<1.0 μm). While it is possible that some pollen was embedded in the contact lens pores, most of the pollutant likely rested on the surface of the lens FIGS. 3A-3D. Results suggest that for large particles (>25 μm), PoPPR is as effective as the RR method.

Conversely, the RR and PoPPR methods differed statistically. FIGS. 5A-5C provide visual representations of results. Both PDMS 1:40 and 1:50 were statistically better at removing microbeads from contact lens surfaces than the RR method and PDMS 1:30. Similar to the pollen results, the RR data exhibited large values of a and MR, indicating large vari-ability in this technique which is expected due to the qualitative nature of this protocol.

Nanoparticle cleaning data show the largest improvement in cleaning method performance. The PDMS 1:40 PoPPR was significantly better at cleaning nanoparticles than RR. Similar to pollen and microbeads, RR and PDMS 1:30 methods remove an approximately equal fraction of nanoparticles.

Figure 6:
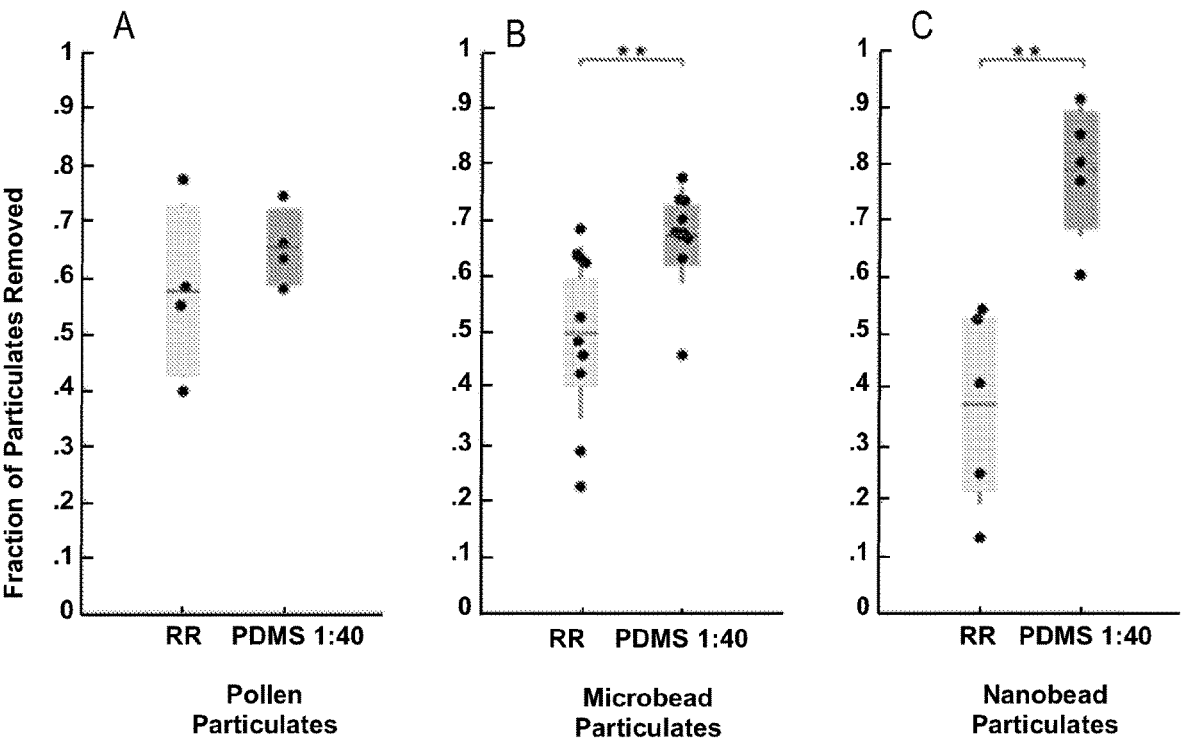
FIGS. 6A-6C show plots of fraction of pollen particulates (FIG. 6A), microbead particulates (FIG. 6B), and nanobead particulates (FIG. 6C) removed from a hydrogel surface after treating with either a solution-based cleaning method or a solvent-free cleaning method and system, in accordance with an exemplary embodiment of the present disclosure.

As shown in FIGS. 6A-6C, the PDMS 1:40 PoPPR method removed more pollutants than the RR method. The control method (RR) and the proposed PoPPR technique were comparable when considering large pollutants (>25 μm). However, the PDMS 1:40 was significantly more successful at small contaminant removal ($PM_{2.5}$) such as microplastics and nanoparticles. During RR removal, the frictional or shearing forces that act on the lens surface are assumed to dislodge particles. These forces may be sufficient for detaching larger particles (pollen), however, for nanoparticles, these forces may not be sufficient. This is attributed further to the rough contact lens surface at the nanometer length scale, where the nanoparticles might be tightly adsorbed on the lens surface. In contrast, the PoPPR technique leverages a normal or extensional peeling force applied to physically detach particles, which works across all size ranges and is surprisingly effective for smaller particles.

The results also suggest that an optimal PDMS stiffness exists that enhances particulate removal from lenses using the PoPPR technique. While the PDMS 1:30 results indicate that there is no statistical significance to RR, 1:30 results are statistically inferior to their PDMS 1:40 counterparts for all pollutants. These results are expected as higher ratio PDMS (≥1:40) are softer (lower Young's modulus) than 1:30, enabling the matrix of PDMS to surround small particles and detach them during peeling. However, the underlying particle removal mechanism based on the PDMS stiffness remains an open question and will be the focus of future work.

Figure 7:
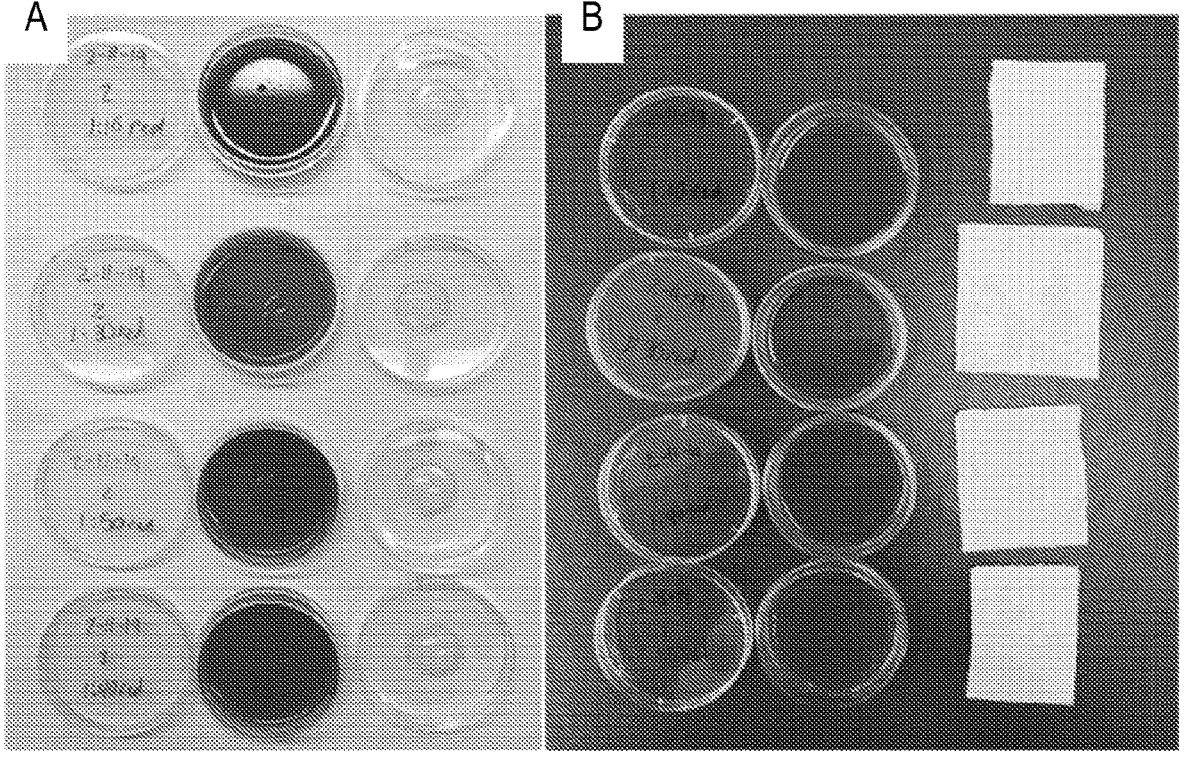
FIGS. 7A and 7B show inertness of various solvent-free cleaning methods and systems, in accordance with an exemplary embodiment of the present disclosure.

A major reason why contact lens cleaning techniques have not changed is that the current method is inexpensive, rapid, and convenient. While rinsing and rubbing is effective for large contaminants, it may negatively impact lens surface integrity (tears, scratches). Additionally, results of the RR method can be highly variable depending on the user. In contrast, the proposed PoPPR technique offers a more efficient, effective, and repeatable pollutant removal technique that utilizes a widely available, inert, and biocompatible polymer (FIGS. 7A and 7B). The PoPPR method may include an extra step in cleaning routines. Different types of contact lens materials can also be used. The PoPPR technique may be beneficial in removing tear film lipid and protein deposits that are often the more common fouling concerns in contact lens wearers. The proof-of-concept cleaning technique presented here has the potential to improve the comfort and long-term use of contact lenses, especially for users in regions with heavy air pollution.

This proof of concept project successfully demonstrated that the PoPPR method for cleaning contact lenses contaminated with different sized contaminants was comparable to or more effective than the traditional method of rinsing and rubbing with lens cleaners. PDMS that has a setting agent to polymer ratio of 1:40 and 1:50 was determined to be the most effective at removing pollutants of all experimental sizes.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. In a cleaning method comprising:

contacting a surface of a material having pollutants in a range of sizes with a transfer media; and transferring at least a portion of the pollutants from the surface via the transfer media;

wherein at least one of:

transferring comprises transferring the pollutants having a size greater than a first size from the surface via the transfer media comprising a solution; or transferring comprises exclusively adsorbing the pollutants having a size less than the first size from the surface of the material to a surface of the transfer media;

the improvement comprising:

contacting the surface of the material with a transfer media comprising a solid polymer substrate having a Young's modulus between about 0.01 MPa to about 0.5 MPa;

transferring at least a portion of the pollutants having a size less than the first size from the surface via an interfacial interaction between the pollutants and the solid polymer substrate; and absorbing at least a portion of transferred pollutants into the solid polymer substrate;

wherein the solid polymer substrate has a stronger interfacial interaction with the pollutants than the interfacial interaction between the pollutants and the material.

2. The improved cleaning method of claim 1, wherein the pollutants having a size less than the first size are too small to be transferred from the surface via the transfer media comprising the solution.

3. The improved cleaning method of claim 1, wherein the improved cleaning method is solution-free.

4. The improved cleaning method of claim 1, wherein the solution is a cleaning solution; and wherein the transferring the pollutants having the size greater than the first size from the surface via the cleaning solution is selected from the group consisting of rubbing the material with the cleaning solution and soaking the material in the cleaning solution.

5. The improved cleaning method of claim 1, wherein the transferring the pollutants having a size greater than the first size from the surface via the solution damages the material; and wherein the transferring at least a portion of the pollutants having a size less than the first size from the surface via the interfacial interaction between the pollutants and the solid polymer substrate leaves the material damage free.

6. The improved cleaning method of claim 1, wherein the interfacial interaction is selected from the group consisting of Van der Waals forces, hydrogen bonding, ionic bonding, ion-induced dipole forces, and ion-dipole forces.

7. The improved cleaning method of claim 1, wherein at least a portion of the transferred pollutants range in size between about 1 mm to about 1000 mm.

8. The improved cleaning method of claim 1, wherein at least a portion of the transferred pollutants range in size between about 5-10 nm.

9. The improved cleaning method of claim 1, wherein at least a portion of the transferred pollutants are selected from the group consisting of pollen, mold spores, lint, fungi, bacteria, wood smoke, cooking smoke, pesticides, herbicides, dust, dust mites, hair, pet dander, auto emission, fiberglass insulation particles, carpet fibers, coal dust, asbestos dust, insecticide, microbeads, and combinations thereof.

10. The improved cleaning method of claim 1, wherein at least a portion of the transferred pollutants are selected from the group consisting of viruses, sub-pollen, suspended atmospheric dust, asbestos, smog, oil smoke, tobacco smoke, volatile organic compounds, nanobeads, nanoparticles, and combinations thereof.

11. A cleaning method comprising:

contacting a surface of a material having particulates directly with a solid polymer substrate having a Young's modulus between 0.01 MPa to 0.5 MPa and a crosslinked matrix positioned on at least one surface of the solid polymer substrate; and absorbing at least a portion of particulates into the crosslinked matrix of the solid polymer substrate.

12. The method of claim 11, wherein the solid polymer substrate comprises PDMS with a polymer-to-setting agent of from 1:30 to 1:50, and a Young's modulus of 0.5 MPa.

13. The method of claim 11, wherein the crosslinked matrix comprises micron and/or sub-micron pores.

14. The method of claim 11, wherein the material is a dry material.

15. The method of claim 11 further comprising absorbing at least a portion of the particulates when the material is a moist material.

16. The method of claim 11, wherein the absorbing the at least a portion of the particulates into the crosslinked matrix does not damage the material.

17. The method of claim 11, wherein the material comprises a hydrogel.

18. The method of claim 11, wherein the material is selected from the group consisting of a moist material, a damp material, a watery material, and combinations thereof.

19. The method of claim 11, wherein the particulates comprise sub-micron particulates.

20. The method of claim 11, wherein at least a portion of the solid polymer substrate is translucent.

21. The method of claim 11 further comprising emitting disinfecting light on at least a portion of the surface of the material.

22. The method of claim 11, wherein the solid polymer substrate comprises an inert biocompatible polymer.

23. The method of claim 22, wherein the inert biocompatible polymer is selected from the group consisting of polyethylbenzene, polydimethylsiloxane (PDMS), polyglycolic acid (PGA), poly-L-lactic acid (PLA), polycaprolactive, polyhydroxybutyrate, polyhydroxyvalerate, polydioxanone, polycarbonate, and polyanhydride, polycaprolactone (PCL), polydioxanone (PDO), polybutyrolactone (PBL), polyvalerolactone (PVL), poly(lactide-co-glycolide) (PLGA), and combinations thereof.

24. The method of claim 11, wherein the absorbing the at least a portion of the particulates comprises transferring at least a portion of the particulates from the surface via an interfacial interaction between the particulates and the solid polymer substrate; and wherein the solid polymer substrate has a stronger interfacial interaction with the particulates than the interfacial interaction between the particulates and the material.

25. The method of claim 24, wherein the interfacial interaction is selected from the group consisting of Van der Waals forces, hydrogen bonding, ionic bonding, ion-induced dipole forces, and ion-dipole forces.

26. The method of claim 24, wherein at least a portion of the transferred particulates range in size between about 1 mm to about 1000 mm.

27. The method of claim 24, wherein at least a portion of the transferred particulates range in size between about 5-10 nm.

28. The method of claim 24, wherein at least a portion of the transferred particulates are selected from the group consisting of pollen, mold spores, lint, fungi, bacteria, wood smoke, cooking smoke, pesticides, herbicides, dust, dust mites, hair, pet dander, auto emission, fiberglass insulation particles, carpet fibers, coal dust, asbestos dust, insecticide, microbeads, and combinations thereof.

29. The method of claim 24, wherein at least a portion of the transferred particulates are selected from the group consisting of viruses, sub-pollen, suspended atmospheric dust, asbestos, smog, oil smoke, tobacco smoke, volatile organic compounds, nanobeads, nanoparticles, and combinations thereof.

30. A cleaning system a cleaning method comprising contacting a surface of a material having particulates directly with a solid polymer substrate having a Young's modulus between 0.01 MPa to 0.5 MPa and a crosslinked matrix positioned on at least one surface of the solid polymer substrate, and absorbing at least a portion of particulates into the crosslinked matrix of the solid polymer substrate, the cleaning system comprising:

the solid polymer substrate having the crosslinked matrix;

wherein the crosslinked matrix is configured to absorb the particulates when placed in direct contact with the surface of the material.

\* \* \* \* \*